US012714536B2

(12) United States Patent
Freier et al.

(10) Patent No.: US 12,714,536 B2
(45) Date of Patent: Aug. 25, 2026

(54) TISSUE MARKER

(71) Applicant: Surgmark GmbH, Hamburg (DE)

(72) Inventors: Thomas Freier, Mainz (DE); Rivelino Montenegro, Mainz (DE); Frank Schure, Biesenthal (DE); Christine König, Hamburg (DE)

(73) Assignee: SURGMARK GMBH, Hamburg (DE)

( * ) Notice: Subject to any disclaimer, the term of this patent is extended or adjusted under 35 U.S.C. 154(b) by 76 days.

(21) Appl. No.: 18/681,102

(22) PCT Filed: Aug. 3, 2022

(86) PCT No.: PCT/EP2022/071841
§ 371 (c)(1),
(2) Date: Feb. 5, 2024

(87) PCT Pub. No.: WO2023/012223
PCT Pub. Date: Feb. 9, 2023

(65) Prior Publication Data

US 2025/0134618 A1 May 1, 2025

Related U.S. Application Data

(60) Provisional application No. 63/229,079, filed on Aug. 4, 2021.

(51) Int. Cl.
*A61B 90/00* (2016.01)

(52) U.S. Cl.
CPC ...... *A61B 90/39* (2016.02); *A61B 2090/3912* (2016.02)

(58) Field of Classification Search
CPC . A61B 90/00; A61B 90/39; A61B 2090/3912; A61B 2090/3908; A61B 2090/3966; A61B 2090/3987
See application file for complete search history.

(56) References Cited

U.S. PATENT DOCUMENTS

| | | | | |
|---|---|---|---|---|
| 7,972,619 | B2 * | 7/2011 | Fisher | A61B 90/39 424/444 |
| 8,311,610 | B2 | 11/2012 | Ranpura | |
| 2003/0109899 | A1 | 6/2003 | Fisher et al. | |
| 2016/0015475 | A1 | 1/2016 | Jones et al. | |
| 2021/0153872 | A1 * | 5/2021 | Nguyen | A61B 17/12145 |

FOREIGN PATENT DOCUMENTS

| | | | |
|---|---|---|---|
| EP | 1579878 | A1 | 9/2005 |
| WO | 2004026111 | A2 | 4/2004 |

* cited by examiner

*Primary Examiner* — Vi X Nguyen
(74) *Attorney, Agent, or Firm* — McGlew and Tuttle, P.C.

(57) ABSTRACT

A tissue marker for insertion into a human or animal body during a surgical procedure. The tissue marker having a first marker element and at least one second marker element, the first and at least one second marker element contain a biodegradable material. According to the technical solution described the first marker element comprises a hollow body containing chitosan and the second marker element is located inside the hollow body of the first marker element.

20 Claims, 4 Drawing Sheets

15
16
11
10
7
8
1
9
12
6
13
14

1
3
2

1
3
2

1

TISSUE MARKER

CROSS REFERENCE TO RELATED APPLICATIONS

This application is the U.S. national stage of International Application No. PCT/EP2022/071841, filed on 2022 Aug. 3. The PCT application claims the priority of the U.S. provisional application 63/229,079 filed on Aug. 4, 2021.

BACKGROUND

The present invention relates to a tissue marker for insertion into a human or animal body during a surgical procedure. According to the technical solution described the tissue marker comprises a first marker element and at least one second marker element, wherein as well the first as at least one second marker element contain a biodegradable material.

Cancer is a leading cause of death worldwide, accounting for nearly 10 million deaths in 2020. According to the World Health Organization (WHO) in terms of new cases of cancer the most common in 2020 were breast cancer (2.26 million cases), lung cancer (2.21 million cases), colon and rectum cancer (1.93 million cases) and prostate cancer (1.41 million cases). The most common causes of cancer death in 2020 were lung cancer (1.80 million deaths), colon and rectum cancer (935 000 deaths) and liver cancer (830 000 deaths). Breast cancer caused 685 000 deaths worldwide.

Besides avoiding known risks, such as consumption of tobacco, alcohol or drugs, the cancer burden can be reduced through early detection of cancer and appropriate treatment and care of patients who develop cancer. Many cancers have a high chance of cure if diagnosed early and treated appropriately.

Specific types of cancer diagnosis techniques use physical tissue markers to mark certain areas in the body. A tissue marker is inserted into the part of the body under examination, e.g. the breast, either, at the time of a biopsy, or to mark a previously diagnosed abnormality. Different types of tissue markers are available and the tissue marker, also called marker clip, most suitable for the particular requirements of a treatment is used. Known tissue markers vary in material and shape. Sometimes different tissue markers especially tissue markers of different shape are used, when multiple areas in the same part of a body must be marked. In case the area of concern is small and could possibly be fully removed during a biopsy the marker is inserted and will then be visible if further imaging or procedures are required in the future. In other cases, a biopsy is performed with ultrasound and a marker is inserted. Following such a biopsy a mammogram is performed to check if the abnormality visible under ultrasound can be seen with a mammogram. Alternatively, the marker shows where the ultrasound abnormality is in case the mammogram appears normal. Furthermore, when a tissue marker is seen on subsequent mammograms it shows the radiologist where a biopsy has been previously performed and repeated biopsies of the same abnormality are prevented. Finally, sometimes when a cancer is diagnosed a chemotherapy is performed before surgery. In this instance, a marker is placed in the cancer, in close proximity, or in an abnormal lymph node, as these may respond to the treatment and be too small to locate on imaging at a later date. Moreover, should the cancer largely disappear with chemotherapy, the tissue marker will allow to identify its former location with further imaging when the time comes to remove it surgically.

In this context, U.S. Pat. No. 8,311,610 B2 discloses a biopsy tissue marker including a first marker element and a second marker element. The first marker element is configured for detection by a first imaging modality, whereas the second marker element is configured for detection by a second imaging modality different from the first imaging modality.

First and second marker elements are engaged with each other and are both made of non-biodegradable material, for example metal containing material, ceramic material, polymer material or composite material. According to one specific embodiment of the described solution the second marker element has a twisted configuration, which can contain a plurality of loops or cords arranged along the longitudinal axis of the first marker element.

A major drawback of a tissue marker made of non-biodegradable material is that in the majority of instances where a suspicious lesion is detected it remains permanently in the patient's body, e.g. in the breast. Therefore, many patients elect to have it removed if the biopsy turns out a negative result or if the markers remain in the breast even after surgery.

Especially if a non-biodegradable material containing a metal is used another drawback relates to problems due to changes in the local magnetic field during MRI-imaging, that are caused by the paramagnetic and diamagnetic properties of the tissue markers. This can possibly limit the sensitivity of MRI-imaging and the efficiency of follow-up breast-cancer treatments.

As an alternative to the tissue markers described above, tissue markers made of biodegradable material are known. Here, U.S. Pat. No. 7,972,619 B2 describes a tissue marker comprising at least two elements made of biodegradable material. The second marker element is located inside the first marker element, whereas the second marker element is formed of a biodegradable polymer having drug-delivery capabilities. The first marker element as well encapsulates the second marker element and should serve to help anchor the tissue marker against migration.

Furthermore, according to a specific technical solution described the second marker element is treated so that it is visible under ultrasound, magnetic resonance imaging, and other imaging techniques. For this purpose, the second marker element may contain or be impregnated with a contrast solution. In addition, a drug or drugs may be added to the second marker element made of a biodegradable polymer so that said drug or drugs are delivered over time to the patient as the marker degrades.

Irrespective of whether a tissue marker is made of a non-biodegradable or biodegradable material, another drawback includes the migration of the tumor markers away from the biopsy and insertion side immediately after deployment, often including displacement along the track of the biopsy needle.

SUMMARY

Based on the limitations of biomarkers for ultrasonic diagnosis known from the prior art including the problems described above an object of the invention is to provide a new tissue marker that enables safe and gentle procedures in tissue examination, especially in breast cancer diagnostics. In this regard, one major object of the invention is to overcome the drawbacks of biopsy markers made of non-biodegradable material and to provide a biodegradable tissue marker with a degradation rate sufficient for a desired period of follow-up clinical checks, e.g. for few months. This period of degradation should advantageously be adaptable as may be necessary. Furthermore, it is of importance, that a tissue marker is easily visible using the standard imagining methods for cancer diagnosis. Another object of the invention is to provide a tissue marker, which can be used in different areas of the human or animal body for ultrasound-assisted biopsy and tumor resection, and is particularly suitable in the field of breast cancer diagnostics and treatment. Furthermore, the tissue marker to be provided should be safely and reliably distinguishable from the surrounding tissue due to its echogenicity, and it should be possible to insert the tissue marker into the body of a human or animal with the help of biopsy instruments commonly used today.

The above objects are met with a tissue marker according to claim 1, a method according to claim 17 as well as with specific uses of said tissue marker according to claims 18 and 19. Preferred embodiments of the invention are disclosed in the dependent claims and will be explained in detail in the following description. Additionally, certain specific embodiments of the invention are explained with the help of drawings.

DETAILED DESCRIPTION

The invention relates to a tissue marker for insertion into a human or animal body during a surgical procedure comprising a first marker element and at least one second marker element, said first and at least one second marker element containing a biodegradable material. The tissue marker according to the invention is characterized in that the first marker element comprises a hollow body containing chitosan and that the second marker element is located inside the hollow body of the first marker element. Thus, according to the invention, the second marker element or at least one structural component of this marker element is at least partially surrounded and/or encapsulated by the first marker element containing chitosan. Due to the use of chitosan for the first marker element a biodegradable tissue marker is provided, which is highly biocompatible, can easily be produced also in large quantities, and enables high quality ultrasound examinations. Preferably, the first marker element is a chitosan tube whereas the hollow cylindrical interior of the chitosan tube builds a cavity for receiving the second marker element.

The second marker element located inside the first marker element, especially inside a chitosan tube, is designed so that radiation and/or sound, especially ultrasound is reflected in such a way that the second marker element is detectable and distinguishable from as well the first marker element as the surrounding tissue with great precision. Preferably, the second marker element is located within a cavity of the first marker element. Here, for example, the first marker element has a shape like a hollow cylinder, tube, hollow sphere or the like.

Furthermore, it is an advantage when the outer surface of the first marker element made of chitosan is designed so that a close contact between the outer surface of the first marker element and the surrounding tissue mass is ensured as to avoid or at least minimize movements of said tissue marker relative to the tissue. Here, it is possible to coat the outer surface of the first marker element appropriately. Moreover, it is possible to adjust the swelling properties of the first marker element and to increase the outer diameter after marker insertion, thereby ensuring close contact to the surrounding tissue.

According to a specific embodiment of the invention, the second marker element or at least one part of the second marker element is distinguishable as well from the first marker element as from tissue or tumor mass surrounding the first marker element due to its shape, structure, density and/or material composition. Advantageously, the second marker element comprises one element or at least two identical or non-identical elements, e.g. fibres, particles, filaments, tubes, films bands, strips, foam, being arranged within the first marker element, preferably within a cavity at least partly surrounded by the first marker element. Again, it is a main aspect of the invention that the second marker element is precisely detectable using radiation or sound, especially ultrasound, as to localize the tissue marker comprising said second marker element with a high level of accuracy.

In a further particular embodiment not only the first marker element but also the second marker element contains chitosan or at least one chitosan containing material.

Chitosan belongs to a family of polymers made up of N-acetyl-D-glucosamine and/or D-glucosamine subunits. Although occurring in some fungi, chitosan is preferably produced industrially by alkaline hydrolysis of chitin. At degrees of acetylation between 0% and about 60%, the upper limit depending on parameters such as processing conditions, molecular weight, and solvent characteristics, the polymer is soluble in dilute acids at a pH of above 6.3. Oftentimes, the soluble form of the polymer is referred to as chitosan while for the insoluble form the term chitin is used. Chitosan is particularly suitable for tissue markers because of its high biocompatibility, biodegradability and hydrogel properties.

Preferably, at least one of the chitosan compositions disclosed in U.S. Pat. No. 9,771,668 B2 are used to produce the first and/or second marker element according to the invention. Insofar, the disclosure of U.S. Pat. No. 9,771,668 B2 is to be understood as part of this description, as this description takes full advantage of the U.S. Pat. No. 9,771,668 B2.

According to a preferred embodiment of the invention the first marker element and/or the second marker element comprises at least one chitosan component that is dissolvable in an aqueous medium, whereas the solubility is depending on the pH. Furthermore, it is of advantage, when the first marker element and/or the second marker element comprises at least one chitosan component that has a degree of acetylation of either more than 60% or less than 40%.

Moreover, it is conceivable that the first marker element and/or the second marker element comprises non-cross-linked chitosan as a component. According to another embodiment of the invention, the first marker element and/or the second marker element comprises a native chitosan as a component. Still, it is possible that the first marker element and/or the second marker element comprises a combination of chitosan and at least one other polymer, especially at least one biopolymer, which is biocompatible and biodegradable. In another specific embodiment of the invention, the second marker element comprises one or more identical or non-identical elements. Preferably, the second marker element comprises micro-or nano-particles. In addition or as an alternative, the second marker element comprises fibers or filaments, whereas the diameter of at least one of the fibers or filaments is preferably 0.01 mm or more. In another preferred embodiment, the second marker element comprises one or more tubes. In another preferred embodiment, the second marker element comprises one or more films, bands and/or strips. In yet another preferred embodiment, the second marker element comprises a foam.

Using fibers or filaments as part of the second marker element being arranged inside the first marker element is of particular advantage, when the second marker element comprises 1 up to 200 fibers or filaments. Furthermore, it is conceivable that the second marker element comprises at least one radiopaque substance, metal, polymer, radioactive substance, colorant, contrast agent and/or active pharmaceutical agent. According to a preferred embodiment of the invention, the second marker element comprises at least one chemical compound, that serves as suitable contrast agent, for example selected from the group consisting of iodine, barium, or bismuth containing compounds, and all possible combinations thereof.

Alternatively or in addition, the second marker element includes a radioactive substance detectable by a radiation detecting means including a gamma counter and/or a scintillation counter. In another alternative, the second marker element contains a transmitting means adapted to transmit signals in the electromagnetic spectrum that are detectable by receivers adapted to receive signals in the electromagnetic spectrum.

In a further embodiment of the invention, the second marker element located inside the first marker element comprises at least one structural element having specific properties with respect to the reflection of radiation and/or sound, especially ultrasound. Moreover, the second marker element preferably comprises at least one structural element selected from the group consisting of fiber, filament, tube and/or cylinder. In a particular embodiment the second element and/or at least one of the aforementioned structural elements has a helical, spherical, curved and/or spiral shape. Advantageously, a plurality of the aforementioned structural elements are arranged inside the first element building a structure with a specific echogenicity to distinguish the second marker element from the first marker element and the tissue or tumor surrounding the tissue marker by the help of radiation and/or ultrasound imaging. Regarding the design of a structural element located inside the first marker element it is conceivable that multiple fibers or filaments are arranged inside a cavity of the first marker element, for example longitudinally or randomly aligned, crisscross and/or in a clew-shape, in a coiled shape, knitted, woven or non-woven.

A tissue marker according to one of the above-described embodiments of the invention can preferably be used for ultrasound, magnetic resonance imaging and all radioopaque diagnostic techniques. The main idea is to provide a tissue marker which can be produced easily and is made of biocompatible material which after insertion into the body of a human or animal can definitely be detected and degrades in the body of the patient over time. Furthermore, the risk of migration of the marker should be avoided or at least minimized as to the marker should stay in its position.

Furthermore, the invention refers to a method for the diagnosis or treatment of a cancerous disease comprising the steps of inserting a tissue marker according to the invention or at least one particular embodiment of the invention described above into a human or animal body, guiding radiation and/or ultrasound in direction of said tissue marker, detecting radiation and/or ultrasound reflected by said tissue marker with the help of a detecting means, evaluation of the detected radiation and/or ultrasound and localization of the tissue marker on the basis of the evaluation of the detected radiation and/or ultrasound. As well for the evaluation as for the localization preferably an appropriate computer and software running on a computer is used. The resulting information, data and/or image is preferably displayed on a screen.

Another aspect of the invention refers to its specific use. A tissue marker according to the invention is preferably used for ultrasound, magnetic resonance imaging and/or radioopaque diagnostics. Moreover, advantageously the tissue marker according to the invention can be used for marking cancerous tumors.

BRIEF DESCRIPTION OF THE DRAWINGS

Hereinafter, the invention is set forth in more detail on the basis of special embodiments and referring to the figures, without restriction of the general idea of the invention, in which.

DETAILED DESCRIPTION OF THE PREFERRED EMBODIMENTS

Figure 1:
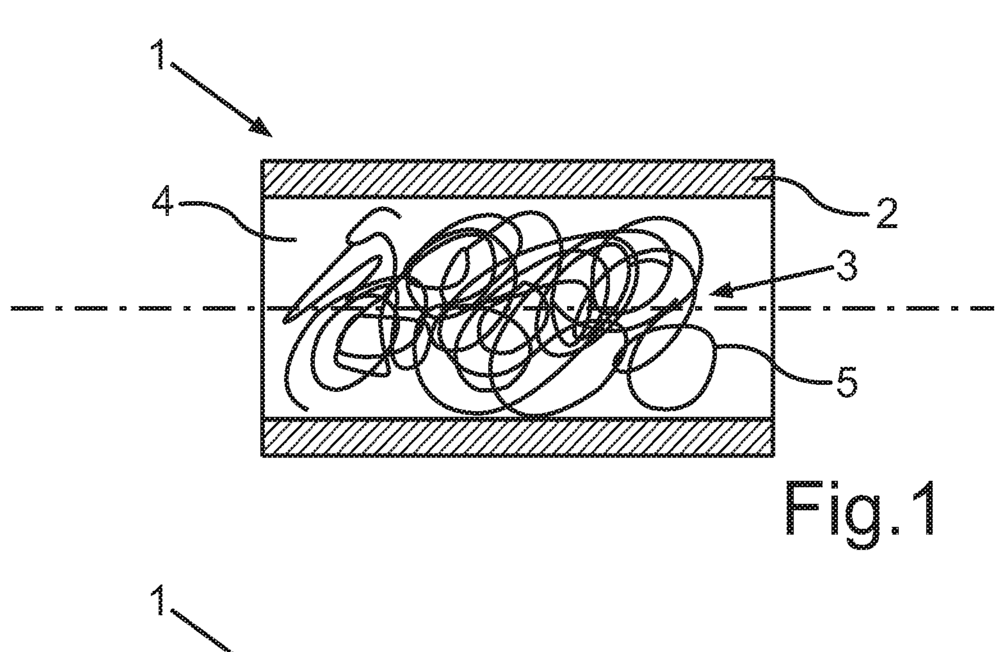
FIG. 1: Sectional view of a tissue marker according to a first embodiment of the invention.

FIG. 1 shows a tissue marker 1 according to the invention in a sectional view. The tissue marker 1 is used for marking a part of patient's body to be examined, especially for the examination or treatment of a cancerous tumor, e.g. in the breast.

The tissue marker 1 shown in FIG. 1 comprises a first and a second marker element 2, 3, whereas the first marker element is a chitosan tube providing a cavity 4 for the second element 3. According to the specific embodiment described, the second marker 3 comprises a structural element 5. Due to the shape and material properties of the structural element 5 the second marker element 3 has a very specific echogenicity, and therefore is clearly distinguishable from the first marker element 2 and the tissue or tumor surrounding the tissue marker 1 when inserted into the body of a human or animal. Because of the specific echogenicity of the second marker element 3 respectively the structural element 5, ultrasound reflected by the structural element 5 results in a very strong and/or specific signal, as the tissue marker can be localized very precisely with the help of ultrasound imaging techniques.

Figure 2:
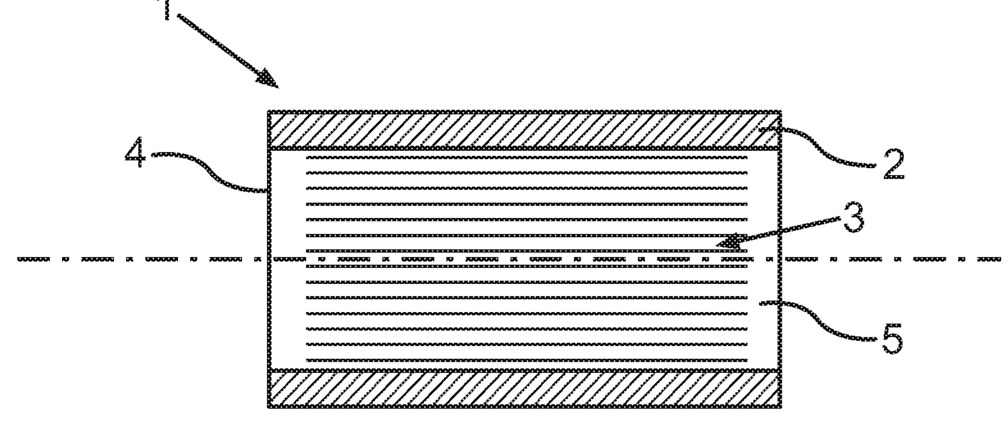
FIG. 2: Sectional view of a tissue marker according to a second embodiment of the invention.

According to FIG. 1 the structural element 5 of the second marker element 3 comprises fibres or filaments made of chitosan arranged crisscross or clew-like inside the first marker element 2. Here, preferably at least 1 and up to 200 fibers or filaments are arranged inside the first marker element. Other types of elements, instead of fibers or filaments, or shape or structures of the second marker element are conceivable. In this context FIG. 2 shows a tissue marker 1 according to a second embodiment of the invention in a sectional view According to FIG. 2 the structural element 5 of the second marker element 3 comprises fibres or filaments, preferably 1 up to 200, made of chitosan, and being longitudinally aligned inside the first marker element 2.

Figure 3:
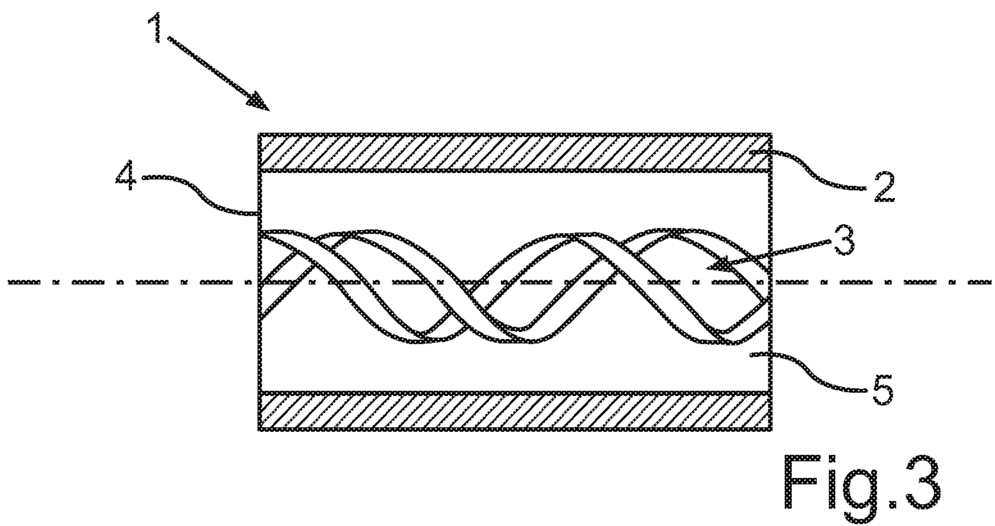
FIG. 3: Sectional view of a tissue marker according to a third embodiment of the invention.

In addition, FIG. 3 shows a third embodiment of the invention in a sectional view. Here, the structural element 5 of the second marker element 3 comprises a film, band and/or strip, preferably 1 to 200, made of chitosan and having a helical shape and being aligned at least partly in longitudinal direction.

Regardless of shape, design an number of second marker elements 3 arranged inside the first marker element 2, the first and the second marker element 2, 3 are made of a chitosan composition. To improve the detectability of the second marker element 3 by using ultrasound, radio-opaque and/or magnetic resonance imagine the second marker element 3 is treated with at least one contrast agent selected from the group consisting of iodine, barium, or bismuth containing compounds, and all possible combinations thereof.

Figure 4:
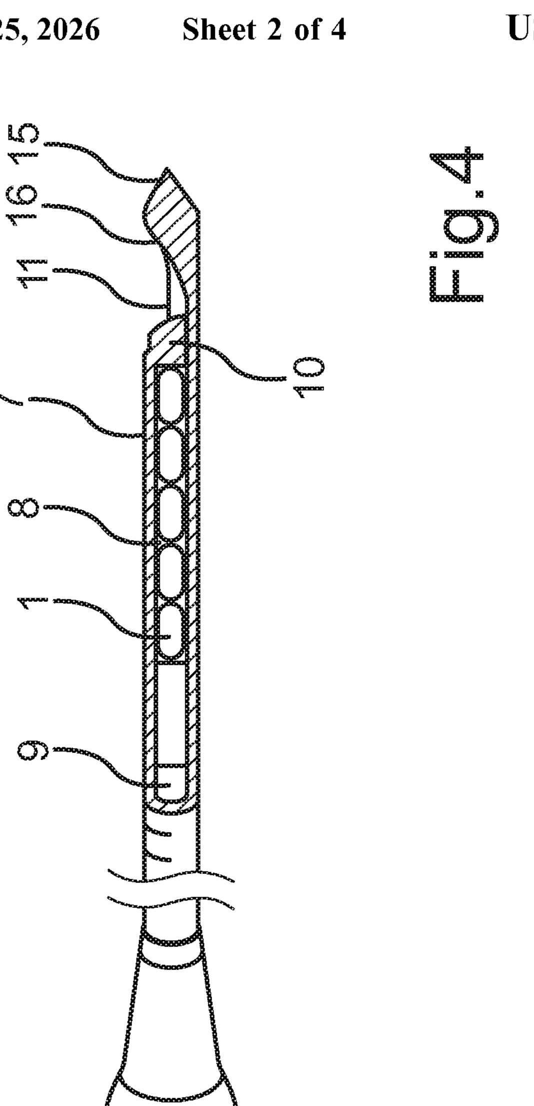
FIG. 4: Partly cut-away perspective view of a tissue marker delivery for the insertion of tissue markers according to the invention into a human or animal body.
Figure 4:
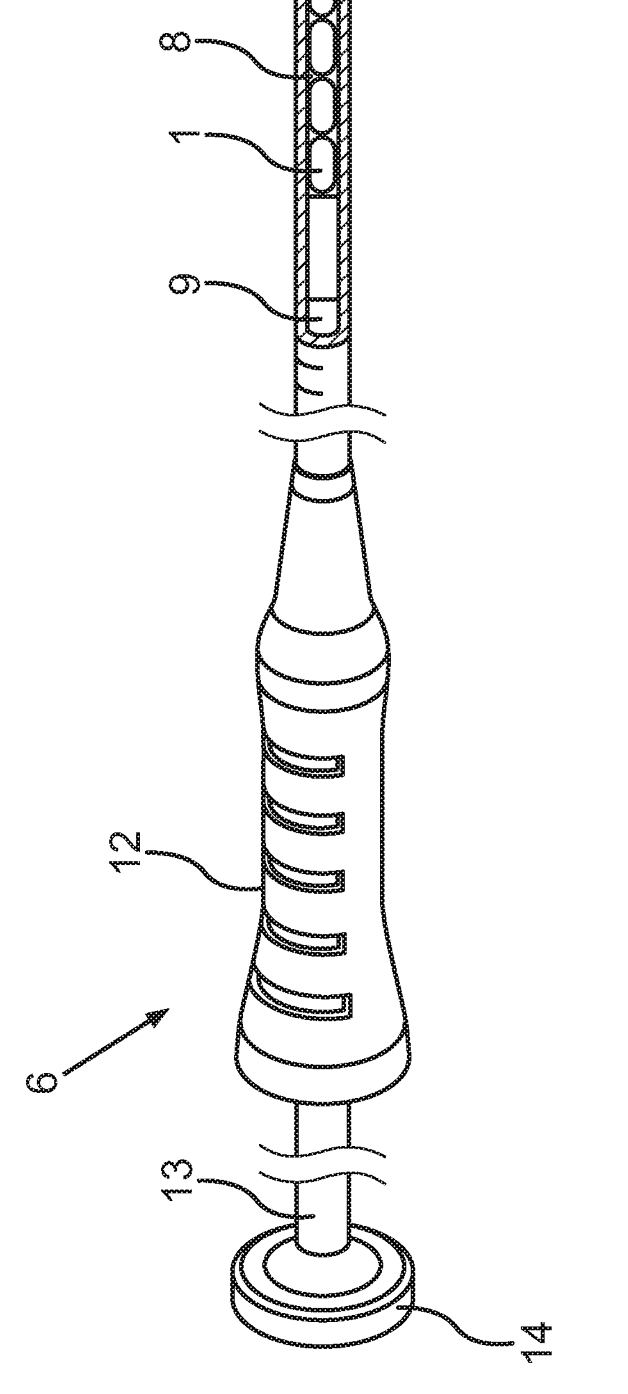

FIG. 4 shows a tissue marker delivery assembly 6. The tissue marker delivery assembly 6 includes a cannula 7 which has an inner lumen 8, a plunger 9 slidably disposed within the inner lumen 8, and a plurality of ultrasonically detectable tissue markers 1 slidably disposed within the inner lumen 8. Moreover, the assembly 6 comprises a plug 10 occluding a discharge opening 11 in the distal portion of the cannula 7.

The delivery cannula 7 has a handle 12 on the proximal end of the cannula shaft 7 to facilitate handling and advancement of the device. The plunger 9 has a plunger shaft 13 and a plunger handle 14 to facilitate advancement of the plunger shaft 13 within inner lumen 8 of cannula 7 to discharge the tissue marker 1 from the discharge opening 11 in the canula 7.

As shown in FIG. 4 a plurality of ultrasonically detectable markers 1 are disposed within the inner lumen 8 distal to the plunger 9. The cannula 7 has a sharp, tissue penetrating distal tip 15 to facilitate advancement through tissue to the target site within the patient. A ramp 16 within the discharge opening 11 of the cannula 7 is provided to guide the tissue markers 1 out through the discharge opening 11.

Figure 5:
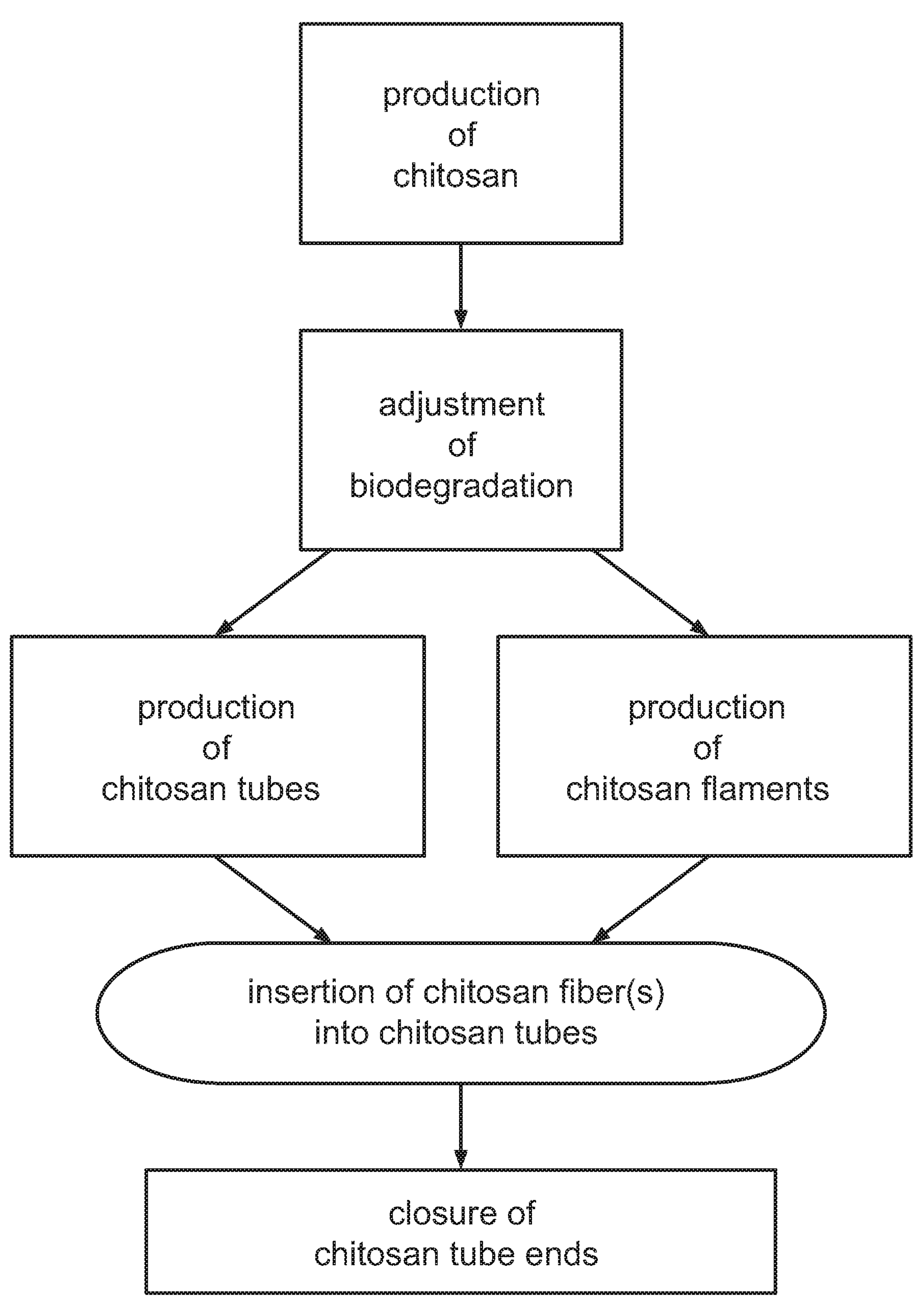
FIG. 5: Method for the production of tissue markers according to the invention.

FIG. 5 shows a detailed process description of a preferred used method for the production of tissue markers according to the invention.

In a first step, chitosan tubes are fabricated as disclosed by "T. Freier et al., Chitin-based tubes for tissue engineering in the nervous system, Biomaterials 2005;26:4624". According to this fabricating method, Chitin hydrogel tubes are synthesized by N-acetylation of chitosan using a twofold excess of acetic anhydride and a cylindrical mold containing a cylindrical core. The resulting tubes show syneresis within 24 h after fabrication, leading to decreased lengths and wall thicknesses. Due to the syneresis the cylindrical core prevents any reduction of the inner diameter of the tube. Advantageously, this technique allows precise control of the resulting chitin tube dimensions.

The fabricated chitosan tubes are mechanically stronger than their chitin origins, as measured by a transverse compressive test. In addition, the compressive strength of chitosan tubes can be increased, either by incorporating reinforcing coils in the tube walls, or air-drying the hydrogel tubes.

Then, in a further step, biodegradation properties of the chitosan tubes can be adjusted by varying the degree if acetylation (DA) as disclosed by "T. Freier et al., Controlling cell adhesion and degradation of chitosan films by N-acetylation, Biomaterials 2005;26:5872". The aforementioned publication shows the results of a systematic in vitro study on the biodegradation and neural cell compatibility of chitosan and N-acetylated chitosan. The in vitro degradation (pH 7.4, 37° C.) in the presence of 1.5 μg/ml lysozyme shows a progressive mass loss to greater than 50% within 4 weeks for chitosan films with 30-70% acetylation. In contrast, the degradation of chitosan samples with very low or high acetylation was minimal over the 4-week period. In this study neural cell compatibility of chitosan and N-acetylated chitosan was tested using primary chick dorsal root ganglion (DRG) neurons. All chitosan-based films showed DRG cell adhesion after 2 days of culture. However, cell viability decreased with increasing acetylation. Chitosan that was 0.5% acetylated had the greatest cell viability, which was approximately 8 times higher than that of chitosan that was 11% acetylated. Chitosan with 0.5% and 11% acetylation showed more and longer neurites than the other samples studied. Thus, chitosan amine content can be tuned for optimal biodegradation and cell compatibility, which are important for the production of tissue marker according to the invention.

Using chitosan fabricated as mentioned before as a basic material, in a further step chitosan fibers or filaments are fabricated as disclosed by U.S. Pat. No. 9,771,668 B2:

According to a preferred embodiment of this production technique 50 ml of a solution of 4% chitosan in 2% acetic acid are mixed with an equal amount of N-methylpyrrolidone (NMP) and filled in a 0.1 liter (L) glass container equipped with a cap containing 2 outlets. One outlet is connected to an air compressor, and the other outlet connects the chitosan solution to a needle of 50 mm in length and an inner diameter of 1.0 mm. The needle is dipped into a coagulation bath containing a mixture of 2 L of NMP and 3 mL of 25% aqueous ammonia solution. The air pressure is adjusted to 490 mbar (490 hPa)±20 mbar (20 hPa), to extrude the chitosan solution into the coagulation bath.

After completion of the extrusion, the fiber is left in the coagulation bath for several hours, e.g. over night. It is then washed in a mixture of distilled water containing 0.1% by weight of a 25% aqueous ammonia solution for 2 hours. For a second washing step, the solution is replaced by a mixture of distilled water containing 0.1% by weight of a 25% by weight aqueous ammonia solution and 1% by weight of glycerol as plasticizer to wash the fiber for another 2 hours. In some experiments, 0.01% by weight of indigocarmine can be added to this mixture for blue staining. After the washing steps, the fiber is removed from the bath, and dried at room temperature while being wound up at a speed of 1 m/min.

Monofilaments of several hundred meters length can be obtained by this method. Moreover, short-length monofilaments, if needed, can be obtained by winding up the monofilament directly on metallic holders being 50 centimeters (cm) apart from each other for drying at room temperature for several hours, e.g. over night. The chitosan monofilaments resulting this way have a diameter of approximately 0.17 mm.

Chitosan monofilaments of different diameters are producible by using needles of different inner diameters.

According to another embodiment of a chitosan fiber or filament fabricating process acetylated chitosan monofilaments are fabricated as described before, except of the drying step. Here, 29.3 g of chitosan monofilaments manufactured as described before, except of the drying step, are treated with 1 L of a 0.01% by weight solution of acetic anhydride in a mixture of NMP/water at a ratio of 60/40 by volume for 2 hours under gentle shaking, and then washed and dried as described before, resulting in an N-acetylchitosan monofilament.

Finally, chitosan fibers or filaments are inserted into chitosan tubes fabricated as described above to build a tissue marker 1 according to the invention, whereby the length of the tissue marker 1 can be adjusted to the particular need. Furthermore, both ends of the chitosan tubes, respectively chitosan tube sections, are closed after insertion of the chitosan filaments. According to this embodiment, the chitosan tube is the first marker element 2 whereas the at least one chitosan fiber arranged inside the chitosan tube is the second marker element 3 of the tissue marker 1. Preferably 1 to 200 chitosan fibers or filaments are arranged inside a chitosan tube, whereby the chitosan fibers or filaments are longitudinally or randomly aligned, arranged crisscross, in a clew-shape, in a coiled shape, knitted, woven and/or non-woven.

Figures 6, 7, 8:
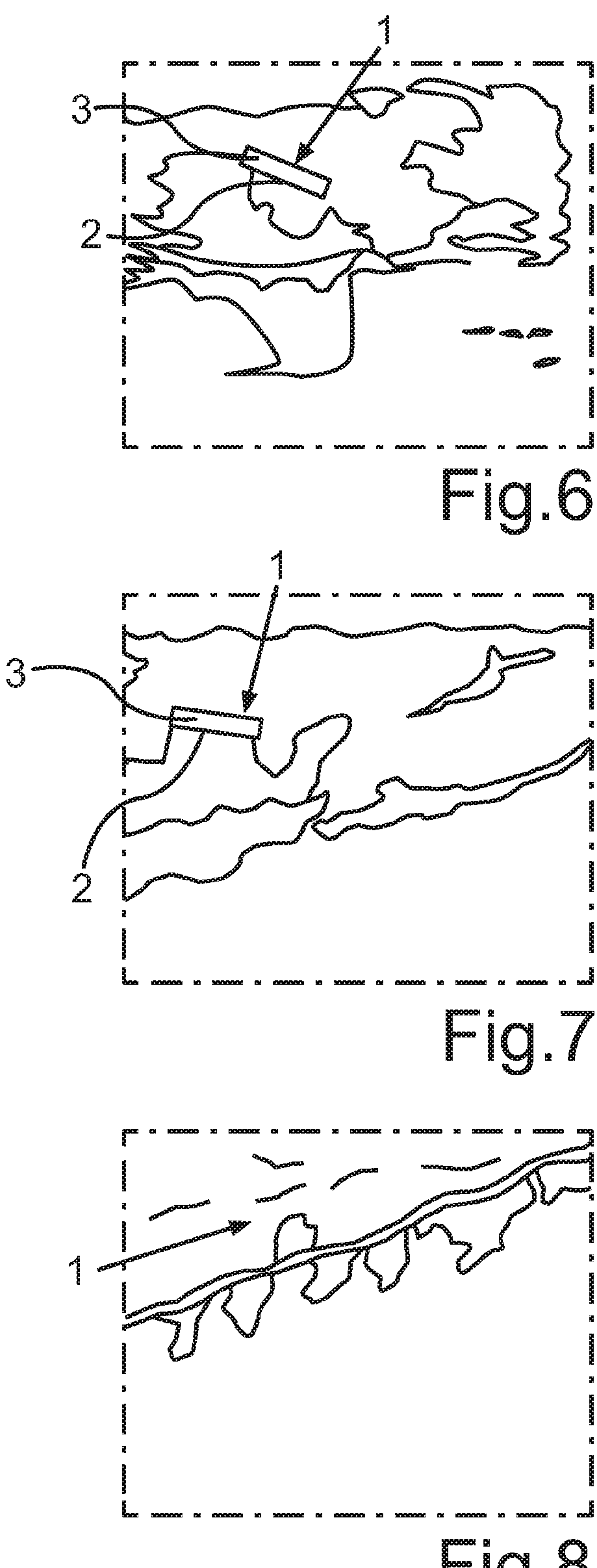
FIG. 6: Sonogram showing a tissue marker according to a first embodiment of the invention located inside a human breast.
FIG. 7: Sonogram showing a tissue marker according to a second embodiment of the invention located inside a human breast.
FIG. 8: Sonogram showing a tissue marker known from the prior art located in a human breast.

To illustrate the differences in echogenicity FIGS. 6 to 8 show sonograms of three different tissue markers located in a human breast two weeks after implantation. The tissue markers shown in FIGS. 6 and 7 are designed according to the invention, and comprise a first marker element 2 and a second marker element 3 located inside the hollow body of the first marker element. The tissue marker shown in FIG. 6 comprises a chitosan tube as first marker element 2 filled with one chitosan filament as a second marker element. Here, the chitosan filament is longitudinally aligned inside the hollow chitosan tube. In addition, FIG. 7 shows a tissue marker 1 according to the invention comprising a chitosan tube as first marker element 2 filled with 15 chitosan filaments as a second marker element 3, said 15 chitosan filaments again are longitudinal aligned inside the hollow chitosan tube.

For comparison, FIG. 8 shows a sonogram of a tissue marker 1 known from the prior art, and commercially available (Scion Medical Technologies) two weeks after implantation in a human breast and it is quite clear, that the echogenicity of the tissue marker 2 known from the prior art is less than the echogenicity of the tissue marker shown in FIG. 6, and even less than the echogenicity of the tissue marker shown in FIG. 7.

LIST OF REFERENCE NUMERALS

1 tissue marker
2 first marker element
3 second marker element
4 cavity of the first marker element
5 structural element
6 tissue marker delivery assembly
7 cannula
8 inner lumen
9 plunger
10 plug
11 discharge opening
12 handle
13 plunger shaft
14 plunger handle
15 distal tip
16 ramp

The invention claimed is:

1. A tissue marker configured for insertion into a human or animal body during a surgical procedure comprising a first marker element and at least one second marker element, said first and at least one second marker element containing a biodegradable material, wherein the first marker element comprises a hollow body containing chitosan, and wherein the second marker element is located inside the hollow body of the first marker element.

2. The tissue marker according to claim 1, wherein the second marker element is distinguishable from the first marker element and/or tissue mass surrounding the first marker element due to its shape and/or echogenicity.

3. The tissue marker according to claim 1, wherein the second marker element comprises at least one chitosan component.

4. The tissue marker according to claim 1, wherein the first marker element and/or the second marker element comprises at least one chitosan component, that is dissolvable in an aqueous medium, the solubility depending on the pH.

5. The tissue marker according to claim 1, wherein the first marker element and/or the second marker element comprises at least one chitosan component that has a degree of acetylation of either more than 60% or less than 40%.

6. The tissue marker according to claim 1, wherein the first marker element and/or the second marker element comprises non-cross-linked chitosan as a component.

7. The tissue marker according to claim 6, wherein a diameter of at least one of the fibers is 0.01 millimeters or more.

8. The tissue marker according to claim 6, wherein the second marker element comprises 1 to 200 fibers.

9. The tissue marker according to claim 1, wherein the first marker element and/or the second marker element comprises a native chitosan as a component.

10. The tissue marker according to claim 1, wherein the first marker element and/or the second marker element comprises a combination of chitosan and at least one other polymer.

11. The tissue marker according to claim 1, wherein the second marker element comprises particles.

12. The tissue marker according to claim 1, wherein the second marker element comprises one or more fibers.

13. The tissue marker according to claim 1, wherein the second marker element comprises one or more films, bands and/or strips.

14. The tissue marker according to claim 1, wherein the second marker element comprises a foam.

15. The tissue marker according to claim 1, wherein the second marker element comprises at least one radio-opaque substance, colorant, metal, polymer and/or active pharmaceutical agent.

16. The tissue marker according to claim 1, wherein the second marker element comprises at least one component having a helical, spherical, curved and/or spiral shape.

17. The tissue marker according to claim 1, wherein the second marker element comprises at least one fiber, tube and/or cylinder having a helical, spherical, curved and/or spiral shape.

18. The tissue marker according to claim 1, wherein the first marker element comprises at least one chitosan tube.

19. Use of a tissue marker according to claim 1 for ultrasound, magnetic resonance imaging and/or radio-opaque diagnostics.

20. Use of a tissue marker according to claim 1 for marking cancerous tumors.

* * * * *